(12) United States Patent
Liu (10) Patent No.: US 7,189,370 B2
(45) Date of Patent: Mar. 13, 2007

(54) APPARATUS AND METHODS FOR HIGH THROUGHPUT AND HIGH-RESOLUTION ASSAYS

(75) Inventor: Shaorong Liu, Lubbock, TX (US)

(73) Assignee: Microchem Solutions, Lubbock, TX (US)

( * ) Notice: Subject to any disclaimer, the term of this patent is extended or adjusted under 35 U.S.C. 154(b) by 216 days.

(21) Appl. No.: 10/371,981

(22) Filed: Feb. 21, 2003

(65) Prior Publication Data

US 2003/0175165 A1    Sep. 18, 2003

Related U.S. Application Data

(60) Provisional application No. 60/383,190, filed on May 23, 2002, provisional application No. 60/359,391, filed on Feb. 22, 2002.

(51) Int. Cl.
| | |
|---|---|
| *B01L 11/00* | (2006.01) |
| *B01L 3/00* | (2006.01) |
| *B32B 5/02* | (2006.01) |
| *B32B 27/04* | (2006.01) |
| *B32B 27/12* | (2006.01) |

(52) U.S. Cl. .......................... 422/101; 422/50; 422/55; 422/58; 422/63; 422/68.1; 422/81; 422/82; 422/100; 422/102; 422/103; 422/104; 436/43; 436/63; 436/164; 436/174; 436/180; 436/177; 436/178; 73/1.01; 73/1.02; 73/53.01; 435/283.1; 435/286.5; 435/286.6; 435/287.1; 435/287.2; 435/287.3; 435/288.4; 435/288.5; 435/288.7; 204/403.01; 204/403.02; 204/403.03; 204/193

(58) Field of Classification Search .................. 422/50, 422/55, 58, 63, 68.1, 81, 82, 100, 101, 102, 422/103, 104; 436/43, 63, 164, 174, 180, 436/177, 178; 73/1.01, 1.02, 53.01; 435/283.1, 435/286.5, 286.6, 287.1, 287.2, 287.3, 288.4, 435/288.5, 288.7; 204/403.01, 403.02, 403.03, 204/193

See application file for complete search history.

(56) References Cited

U.S. PATENT DOCUMENTS

| | | | | |
|---|---|---|---|---|
| 5,872,010 | A * | 2/1999 | Karger et al. | ................ 436/173 |
| 5,954,931 | A * | 9/1999 | Maracas et al. | ............ 204/451 |
| 6,167,910 | B1 * | 1/2001 | Chow | .......................... 137/827 |
| 6,391,622 | B1 * | 5/2002 | Knapp et al. | ............. 435/285.2 |
| 6,468,761 | B2 * | 10/2002 | Yang et al. | .................... 435/23 |
| 6,495,016 | B1 * | 12/2002 | Nawracala | ................... 204/604 |
| 6,602,472 | B1 * | 8/2003 | Zimmermann et al. | ..... 422/100 |
| 6,632,655 | B1 * | 10/2003 | Mehta et al. | ............. 435/288.5 |
| 6,663,833 | B1 * | 12/2003 | Stave et al. | ..................... 422/81 |
| 6,677,114 | B1 * | 1/2004 | Schneider et al. | ............. 435/4 |
| 6,749,734 | B1 * | 6/2004 | Simpson et al. | ............ 204/547 |

* cited by examiner

*Primary Examiner*—Brian Sines
(74) *Attorney, Agent, or Firm*—Liu & Liu (57) ABSTRACT

An apparatus integrates one dimensional separation to another dimensional separation and automates the operation of the two dimensional separation. The first dimensional separation is performed in one column while the second dimensional separation is performed in multiple separation columns. The integration is achieved using a one-piece, a two-piece, or a three-piece interface.

21 Claims, 12 Drawing Sheets

FIG. 8 top block bottom block

To ESI-MS, MALDI-MS TARGET,
fraction collector, or for further digestion

*FIG. 12*

APPARATUS AND METHODS FOR HIGH THROUGHPUT AND HIGH-RESOLUTION ASSAYS

This patent application claims the priority of the following pending applications: U.S. Provisional Patent Application Ser. No. 60/359,391, filed on Feb. 22, 2002; U.S. Provisional Patent Application Ser. No. 60/383,190 filed on May 23, 2002; and U.S. Utility patent application Ser. No. 10/076,012 filed on Feb. 11, 2002.

1. Field of the Invention

The present invention relates generally to the field of high throughput assays of molecules. More particularly, the present invention relates to methods and apparatus of use in multi-dimensional separation of extracts of herbs, plants, organisms/tissues and other natural materials, and protein/peptide samples, using a novel apparatus that integrates one dimension of separation to another dimension of separation.

2. Description of Related Arts

The words "proteome" and "proteomics", related to genome and genomics, were coined in 1995 by a group in Australia. Since the set of genes of an organism is its genome, the set of proteins expressed in a cell is its proteome. Proteomics is the science concerned with the study of proteomes. The major difference between genomes and proteomes is immediately apparent. While the genome is constant between the cell types of an organism and throughout its life span, the proteome is a dynamic entity and varies between cell types and within a cell type, depending on the conditions the cell is facing. This is due to the functional difference between DNA and proteins in the cell. While DNA is the central memory of the cell, coding for the whole repertoire of proteins and RNAs, proteins are the molecular machines of the cell and provide most of the functions the cell needs to live its life.

This statement has several important consequences. First, the proteins show a tremendous chemical heterogeneity in virtually all parameters that can be measured. For example, some mitochondrial proteins weigh 6–8 kD, while giant muscle proteins weigh close to 1000 kD. Some proteins are very soluble and present at high concentrations in water (e.g., albumin, 40 mg/ml in plasma), while some membrane proteins have more than 75% of their amino acids buried in the phospholipid bilayer. This is due to the various functions of the proteins in a cell. Second, proteins are present in extremely divergent concentrations in cells, ranging from 100 to 100,000,000 molecules per cell. It is very important to take into account this wide divergence in abundance. A consequence of the relatively low number of genes encountered in upper organisms is that the difference between cells will probably arise not only from sets of specifically expressed genes, but also (and possible mainly) from quantitative variations between proteins within the same repertoire.

Proteomics must face the formidable challenge of measuring quantitatively the proteins present in the object of interest, while coping with the tremendous chemical diversity of the proteins. To further complicate the task, it is now well known that the activity of many proteins is modulated by posttranslational modifications.

2-D gel electrophoresis was the first that was able to achieve proteomic analysis. The first 2-D separations are attributed to the work of Smithies and Paulik (*Nature*, 1956, 177, 1033) for a 2-D combination of paper and starch gel electrophoresis for the separation of serum proteins. Subsequent developments in electrophoretic technology, such as the use of polyacrylamide as a support medium and the use of polyacrylamide concentration gradients were rapidly applied to 2-D separations. In particular, the application of IEF (isoelectric focusing) techniques developed by O'Farrell (*J. Biol. Chem.*, 1975, 250, 4007–4021) to 2-D separations made it possible for the first dimensional separation to be based on the charge properties of the proteins. The coupling of IEF with SDS-PAGE (sodium dodecyl sulfate-polyacrylamide gel electrophoresis) in the second dimension resulted in a 2-D method that separated proteins according to two independent parameters, isoelectric point and molecular weight. This methodology was then adapted to a wide range of samples with differing solubility properties by the use of urea and applied to the analysis of protein mixtures of whole cells and tissues.

IEF-SDS-PAGE is by far the most popular format for 2-D separation of proteins. This is due to its power to separate thousands of proteins on a single gel, the subsequent high-sensitivity visualization of the resulting 2-D separations that are amenable to quantitative computer analysis to detect differentially regulated proteins, and the relative ease with which proteins from 2-D gels can be extracted for further characterization by sequence analysis or mass spectrometry.

Limitations inherently associated with IEF-SDS-PAGE are the extensive sample handling, nonlinear response factors for the most commonly used staining techniques, limited loading capacity, low extraction efficiencies of the gel-embedded proteins, and a decreasing resolving power for proteins with molecular mass of less than 15 kDa as a result of their high mobility in the gel. Furthermore, it is difficult to isolate proteins with a pI at the acidic and basic extremes of the pH gradient, proteins with molecular weight of higher than 200 kDa, or membrane and other hydrophobic proteins. In addition, the technique is time-consuming, difficult to automate, and challenging for on-line coupling to mass spectrometric detection.

Various 2-D separations can be performed with a combination of two chromatographic methods with different separation mechanisms such as ion exchange, reversed-phase, hydrophobic interaction, and size-exclusion chromatography. Most approaches to 2-D HPLC involve some sort of fraction collection from the first chromatographic column followed by a reinjection of the collected material onto a second column. In off-line techniques, the fractions are collected in vials and reinjected on the second column at a later time. In on-column techniques, a switching valve is used to do one of the following: trap first column effluent containing the region of interest for reinjection directly onto the second column or to direct flow from the first column directly onto the head of the second column during a specific time frame.

A discontinuous 2-D liquid-phase separation method (Wall, D. B., et al. *Anal. Chem.* 2000, 72, 1099–1111) has been published in which proteins in cell lysates were separated using isoelectric focusing in the first dimension followed by fast reversed-phase HPLC in the second dimension. The results obtained by the 2-D system were complementary to that of IEF-SDS-PAGE and improved results were obtained for lower mass and basic proteins. Off-line 2-D HPLC has been automated as well (Vissers et al., *J. Microcolumn Sep.* 1999, 11(4), 277–286).

To analyze all effluent from the first dimension, a comprehensive 2-D HPLC was developed (Bushey and Jorgenson, *Anal. Chem.* 1990, 62, 161–167). This technique was further developed using two parallel reversed-phase columns, rather than storage loops, for sample transfer into the second dimension (Opiteck, et al., *Anal. Chem.* 1997, 69, 2283–2291). However, the challenge for 2-D HPLC separation is that the separation speed of the second dimension is required to be considerably faster than the first one in order to obtain complete 2-D information, which limits the selection of chromatographic modes that can be used for the second-dimensional separation.

In a recent article (Chen, X., et al., G. M. *Anal. Chem.* 2002, 74, 1771–1778), the authors attempted to integrate two dimensional separations for protein separations. Their approach has integrated the 2-D separation but automation of the described operations is virtually impossible.

This invention describes an apparatus that integrates one dimensional separation with another dimensional separation and its operation can be automated. The first dimension can be IEF or HPLC (high performance liquid chromatograph) separation. The second-dimension is parallel-channel CGE (capillary gel electrophoresis), CE (capillary electrophoresis) or CEC (capillary electrochromatograph) that is directly incorporated with the first-dimensional separation. Compared to the current separation techniques for proteomics, the proposed approach has four significant features. First of all, the 2-D separation system can be fully automated, no matter whether the first separation dimension is IEF or HPLC. Secondly, the detection sensitivity will be improved and the separated proteins may be quantified. Thirdly, the second-dimensional separation can be further integrated with MS for the third-dimension separation or characterization. Most importantly, the proteome research will be accelerated and the overall cost for proteomic analysis will be reduced after using such an automated multi-dimensional separation and analysis system. In addition, when the first separation dimension is HPLC, the proposed approach eliminates the speed requirement that the separation of the second dimension should be considerably faster than that of the first dimension. In conventional continuous 2-D separations, this is required in order to obtain meaningful 2-D separation results. Often, separation of the first dimension is deliberately slowed down and stopped-flow technique is often used in order for the second-dimension to catch up. This strategy not only reduces the overall throughput but also sacrifices the resolution of the first separation dimension. Our approach eliminates this requirement because the separation "speed" of the second dimension is picked up through parallel-channel operations.

SUMMARY OF THE INVENTION

The present invention solves a long-standing need in the art by providing an integrated and automated apparatus for high speed, high throughput, high resolution and high sensitivity assays of protein and peptides samples of proteomics. The apparatus can be used for variety of applications, including extracts of herbs, plants, organisms/tissues and other natural materials, microorganisms, DNA, RNA, carbohydrates, polysaccharides and lipids.

In one aspect of the present invention, the first dimension separation, such as IEF, is performed in a tube and the separated bands in the tube can be automatically transferred to the separation column in the second separation dimension for separation. The first and second separation dimensions are integrated.

In one particular embodiment, the integration interface has 3 pieces. The middle piece moves relatively to the top and bottom pieces to facilitate the sample bands transfer from the first separation dimension to the second separation dimension.

In additional embodiment, pH gradient is formed in the interface by delivering a series of solutions having different pH into an IEF separation channel.

In another embodiment, the integrated device has 2 pieces. The top piece moves relatively to the bottom piece to facilitate the sample bands transfer from the first separation dimension to the second separation dimension.

In an additional embodiment, one or more of the above said pieces can be micromachined. In another embodiment, the above said pieces can be made of glass, plastic and other polymeric materials, such as PTFE (polytetrafluoroethylene), Nylon, PVC (polyvinyl chloride), PMMA (poly(methyl methacrylate)), polycarbonate, polystyrene, polypropylene, nitrocellulose, poly(ethylene terephthalate).

In one preferred embodiment, the tube to perform the first dimension separation is curved and contains repeated units to hold the separated bands of the first dimension separation. These repeated tube units are inserted into an array of separation columns to perform the second dimension separation.

In another embodiment, the separated bands of the second dimension separation are further delivered to a detection system, such as MALDI-MS and ESI-MS, a fraction collector, or a device for further chemical reaction, such as protein digestion.

In another aspect of the present invention, the effluent of the first dimension separation, such as HPLC, SEC (size exclusion chromatograph), IC (ion-exchange chromatogaph) and affinity chromatograph, flows into a tube having repeated units that can be incorporated into multiple separation columns to perform the second dimension separation.

In a particular embodiment, when part of the above said effluent is being separated in the second separation dimension, another part of the effluent is flowing into another tube having another set of repeated units that can be incorporated into another set of multiple separation columns to perform the second dimension separation.

In another embodiment, the integration interface has only one piece. The partially separated sample from the first separation dimension is sequentially introduced into the separation columns of the second separation dimension.

Other objects, advantages and salient features of the invention will become apparent to those persons skilled in the art upon reading the following detailed description, which taken in conjunction with the annexed drawings, disclosed preferred embodiments of the invention.

DETAILED DESCRIPTION OF THE INVENTION

Figure 1:
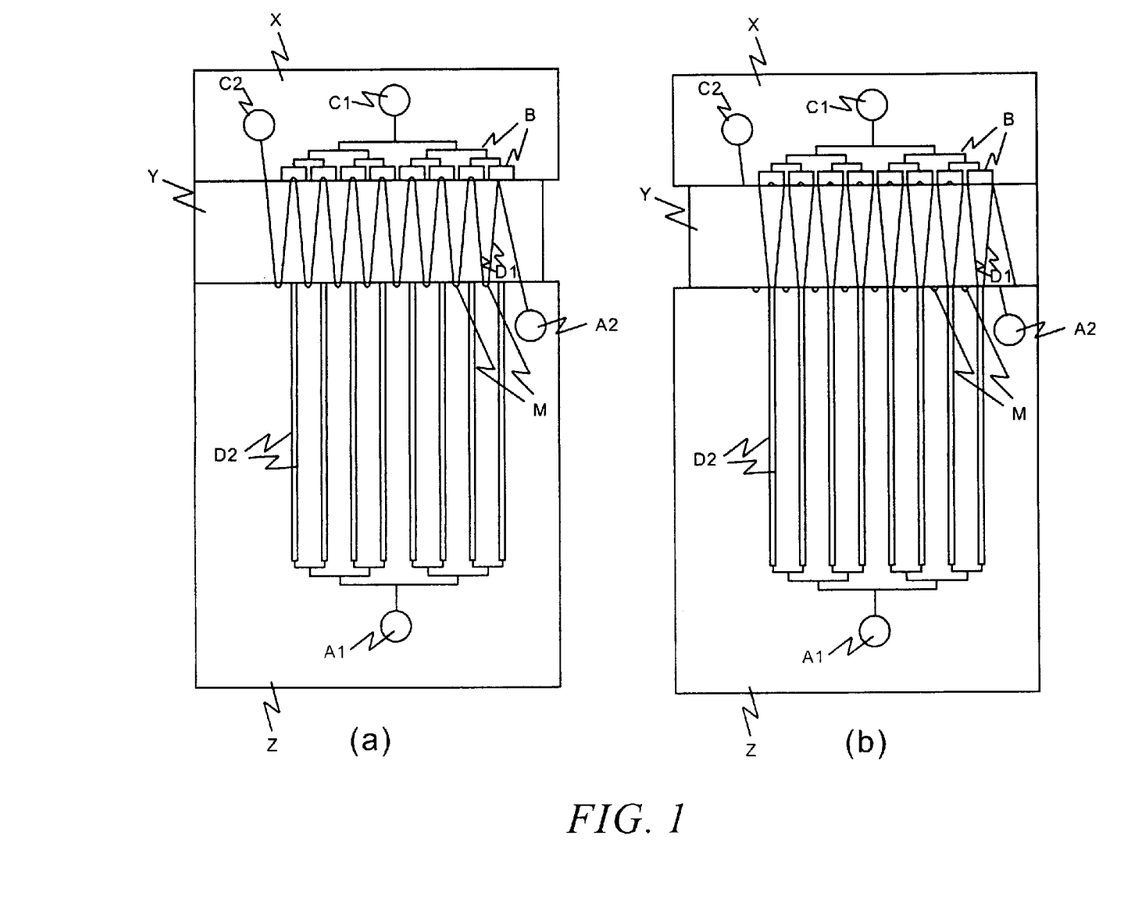
FIG. 1. A schematic representation of an integration interface that comprises three pieces FIG. 2. A schematic representation of an integration interface that comprises two pieces FIG. 3. A schematic representation of an integration interface in which pH gradient is created and replenished within the device FIG. 4. A schematic representation of an integration interface (3-piece) in which the pre-separated sample from the first separation dimension is continuously introduced to the separation columns of the second separation dimension FIG. 5. A schematic representation of an integration interface (2-piece) in which the pre-separated sample from the first separation dimension is continuously introduced to the separation columns of the second separation dimension FIG. 6. A schematic representation of an integration interface (3-piece) that comprises a rotor FIG. 7. A schematic representation of the formation of a rotor FIG. 8. A schematic representation of a rotary integration interface (3-piece) in which the pre-separated sample from the first separation dimension is continuously introduced to the separation columns of the second separation dimension FIG. 9. A schematic representation of a rotary integration interface (2-piece)

The present invention provides an integrated and automated apparatus for high speed, high throughput, and high resolution assays of complex samples, such as herb extracts and protein/peptides samples from proteomic field. In one embodiment, IEF (the first separation dimension) and CGE, CE or CEC (the second separation dimension) is integrated using an interface as shown in FIG. 1. The interface comprises of three separate pieces, X, Y and Z. Preferably, pieces X and Z are fixed in position, while the middle piece, Y, is shifted back and forth between positions indicated in FIGS. 1a and 1b. When the middle piece Y is set at a position as shown FIG. 1a, channels D1 are connected by channels M on pieces X and Z to form a single continuous channel from A2 to C2. IEF may be performed in this channel. After IEF is complete, the middle piece Y is shifted to another position as indicated in FIG. 1b, the continuous channel is segmented into many smaller channels D1 that are inserted between cathode channels B and separation channels D2. Subsequently, the IEF separated bands in channels D1 are all injected into the separation channels D2 for the second-dimensional separation.

Channels M are preferred small since samples in these channels are not used for separations. A1, A2, C1 and C2 are reservoirs to hold buffers and electrodes to facilitate the separations. Preparation for the second-dimensional separation is carried out when the middle piece Y is in the FIG. 1b position.

D1 channels can be short to prevent more than one separated bands in any D1 channel. The downside of short D1 channels is the fragility of the sliding piece Y and the relatively increased volume of the unused solutions in channels M. D1 channels are preferred to be longer than 100 µm, more preferably longer than 500 µm, and more preferably longer than 1 mm. As long as the separation channel is adequately long and the pH range to perform IEF is adequately narrow, that is, dpH/dx is adequately low, each D2 channel will not contain more than one separated IEF bands. When D1 channel length is increased, the width of the middle piece Y may be increased to improve its fragility. At the same time, the quantity of protein sample used for IEF may be increased and, combined with the increased D1 channel length, sample stacking may be amplified for SDS-PAGE to improve the protein detectability.

D2 channels can be conventional capillaries affixed to the bottom piece Z. These capillaries will be combined off the bottom piece Z, and so will be A1 electrode. Alternatively, D2 channels can be micromachined in an analytical chip as schematically presented in FIG. 1.

In an additional embodiment, one or more of the above said pieces can be micromachined. In another embodiment, the above said pieces can be made of glass, plastic and other polymeric materials, such as PTFE (polytetrafluoroethylene), Nylon, PVC (polyvinyl chloride), PMMA (poly(methyl methacrylate)), polycarbonate, polystyrene, polypropylene, nitrocellulose, poly(ethylene terephthalate).

Figure 2:
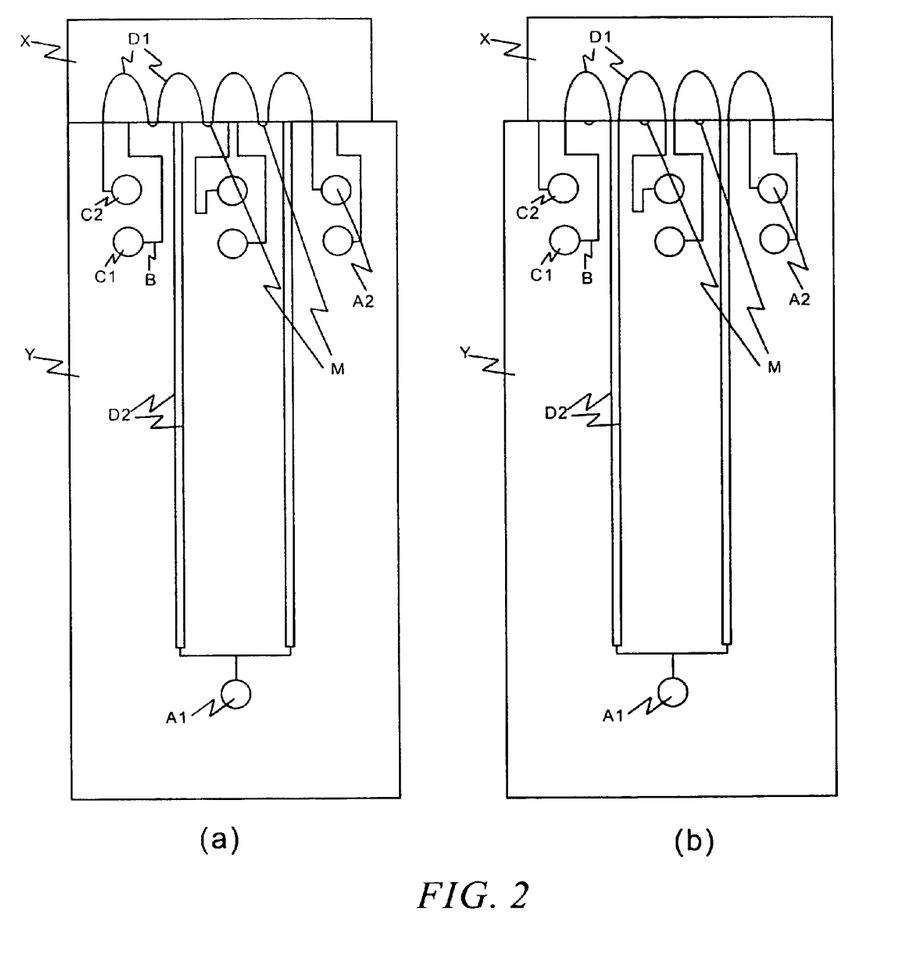

In another embodiment, the interface is modified as schematically represented in FIG. 2 to comprise two separate pieces X, and Y, but perform the same function. When the interface is aligned as shown in FIG. 2a, channels D1 are connected by channels M into a continuous channel from A2 to C2. IEF may be performed in this channel. After IEF is done, the top piece X is switched to another position as shown in FIG. 2b. The continuous channel is segmented into many smaller channels D1 that are inserted between cathode channels B and separation channels D2. The IEF separated bands in channels D1 are injected into the separation channels D2 for the second-dimensional separation.

IEF is a steady state separation method and band broadening caused by varying channel geometries in IEF should not be as significant as that in non-steady-state separation methods. In FIGS. 1 and 2, when the channel length of each D1 fragment is longer than 1 mm, multiple IEF separated bands may be present in one such channel. IEF resolution is lost when multiple separated bands are re-injected into a single channel for the 2-D separation. To alleviate this problem, one can increase the channel length (and hence decrease dpH/dx) for IEF so that each protein band will be increased to be about or more than 1 mm.

Figure 3:
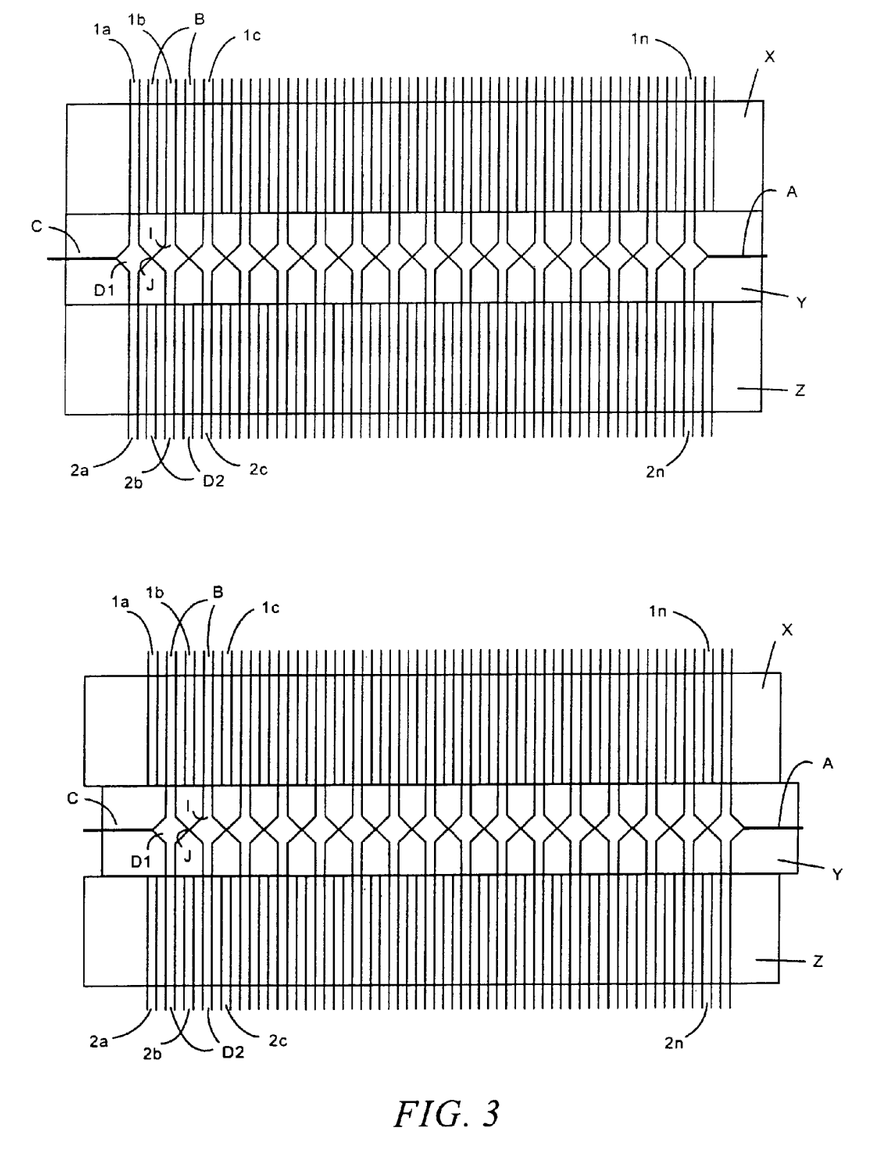

Ampholytes are usually used in IEF to create a pH gradient. These chemicals are pretty expensive and extreme low and high pH gradients are difficult to achieve with ampholytes. In particular embodiment, the FIG. 1 presented interface can be modified to that as shown in FIG. 3 in which any kind of pH gradient can be obtained conveniently and inexpensively. A series of pH solutions, from very high pH (>13) to very low pH (<2), are prepared with pH increments of smaller than 1, preferably smaller than 0.1, or even smaller than 0.01. Once a pH range is selected to perform IEF, the pH solutions within this range are picked up and delivered to the IEF separation channel (formed by D1 fragment channels) respectively through channels 1a, 1b, 1c, . . . and 1n. Solution in channel 1a may be either the high-end or the low-end of the pH solutions, depending on the protein/peptide samples. Therefore, either an increasing or a decreasing pH gradient can be formed in IEF separation channel. Protein/peptide sample can be introduced into the first D1 channel through channel 1a. The sample solution can have a pH that is the same as that of the solution delivered in channel 1a. Preferably, the pH should be slight higher than that of solution in channel 1a if the solution in channel 1a has the high-end pH. Otherwise, the pH should be slightly lower than that of the solution in channel 1a. After all solutions are properly delivered to D1 channels, all solution flows should be stopped. A voltage is applied across D1 channels through C and A channels, and IEF is performed. The middle piece Y is then switched to another position as shown in the bottom figure in which the intersecting channels on D1 are aligned with B and D2 channels.

Partially separated sample in D1 channels can then be injected to D2 channels to perform the second dimensional separation.

In one embodiment, the sample may also be introduced to one of the D1 channels through any of the channels $1a$, $1b$, $1c$, ... $1n$, depending on the pH of the sample solution. Preferably, the sample solution should be introduced through a channel in which the solution pH is closest to that of the sample solution.

In additional embodiment, D1 channels can be simply a straight channel having a vertical intersecting channel. Preferably, the vertical intersecting channel is somehow swollen when intersecting with the horizontal channel. In FIG. 3, these intersecting channels are swollen triangularly. Other forms of swelling schemes, such as smoothly curved shapes, can also be used to reduce the injection dead-volumes for the second dimensional separation. D1 channel width J can be larger than 1 mm. Preferably it should be smaller than 500 µm, more preferably smaller than 200 µm. Intersecting channel width I should be comparable to or smaller than that of the channels in pieces X and Z. The dimension of channels in pieces X and Z ranges from 5 µm to 1000 µm.

Figure 4:
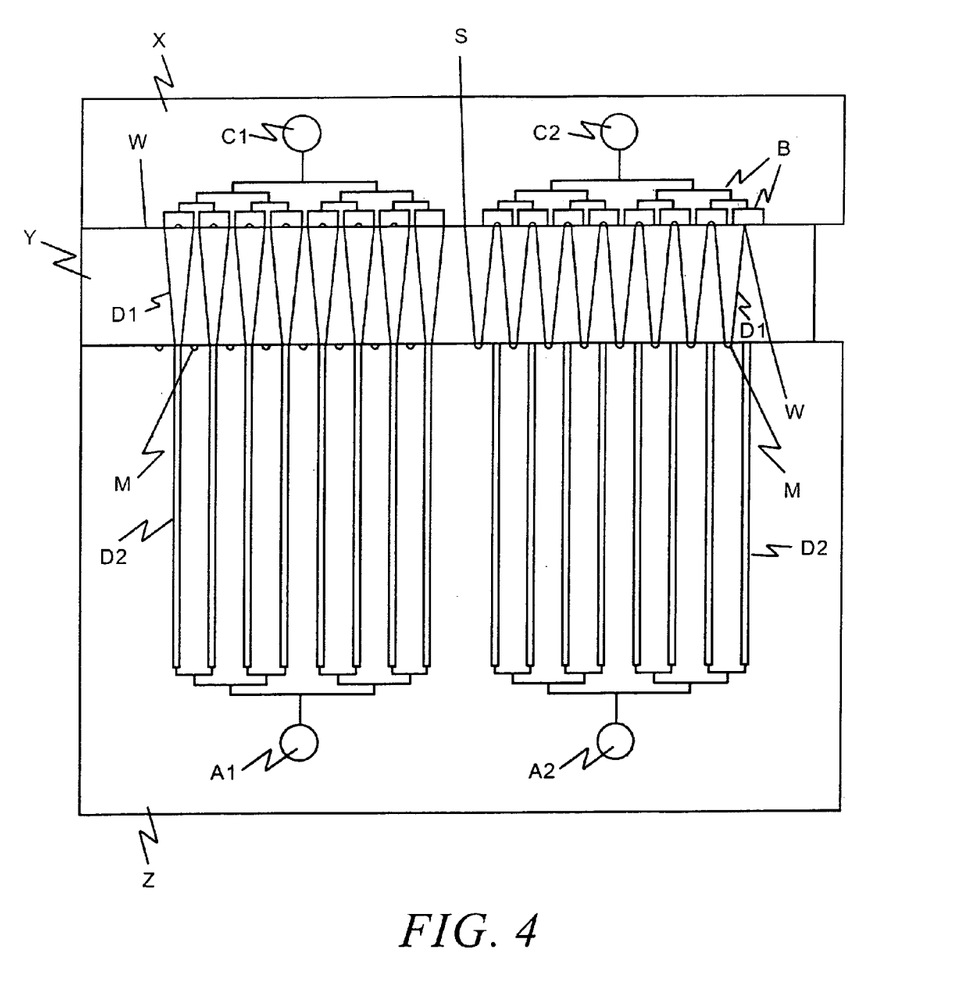

In another embodiment, the device in FIG. 1 is slightly modified to FIG. 4 to integrate HPLC as the first separation dimension to CGE, CE or CEC as the second separation dimension for continuous 2-D separation. The structure pattern is similar to that of FIG. 1, but HPLC (the first-dimensional separation) is performed off the FIG. 4 presented interface. Referring to FIG. 4, HPLC effluent S flows into the continuous channel (composed by the repeating units of D1 and M channels) on the right-hand side. As the effluent front approaches the last D1 channel (before entering waste container W), the middle piece Y is switched right to another position (figure not shown). The continuous channel on the right-hand side is broken into pieces of D1 and M channels and D1 channels are inserted between cathode channels B and separation channels D2. HPLC separated bands in D1 channels are injected into the D2 channels on the right-hand side for the second-dimensional separation. Meanwhile, channels D1 and M on the left-hand side are connected into a continuous channel and the effluent S is directed into this channel. As the effluent front approaches the last D1 channel (before entering waste container W) on the left-hand side, the middle piece Y is switched left to the original position (FIG. 4). The HPLC separated bands in the D1 channels on the left-hand side are injected into the according D2 channels for the second-dimensional separation. These operations are repeated until the completion of the HPLC (the first-dimensional) separation.

The number N of columns for the second-dimensional separation can be calculated based on the flow rate f of the first separation dimension and the separation speed r (unit in min/separation) and injection volume v of the second separation dimension.

$$N=f*r/v$$

Assuming that the flow rate of the first-dimensional separation, such as capillary HPLC, is 0.5 µL/min, the second-dimensional separation needs 2 min to complete and the injection volume is 20 nL. Referring to FIG. 4, the middle piece Y will be switched in every two min and the continuous channel needs to hold 1 µL effluent. Because the sample injection volume is 20 nL for each separation channel, therefore, 50 separation channels on each side of the device will be required to distribute the 1 µL effluent to fulfill the second-dimensional separation. That is, $$N=0.5(µL/min)*2(min)/20(nL)=50.$$

Assuming the separation speed of the first-dimensional separation is R (unit in min/separation), the total number n of the second-dimensional separations is $$n=N*R/r$$

Figure 5:
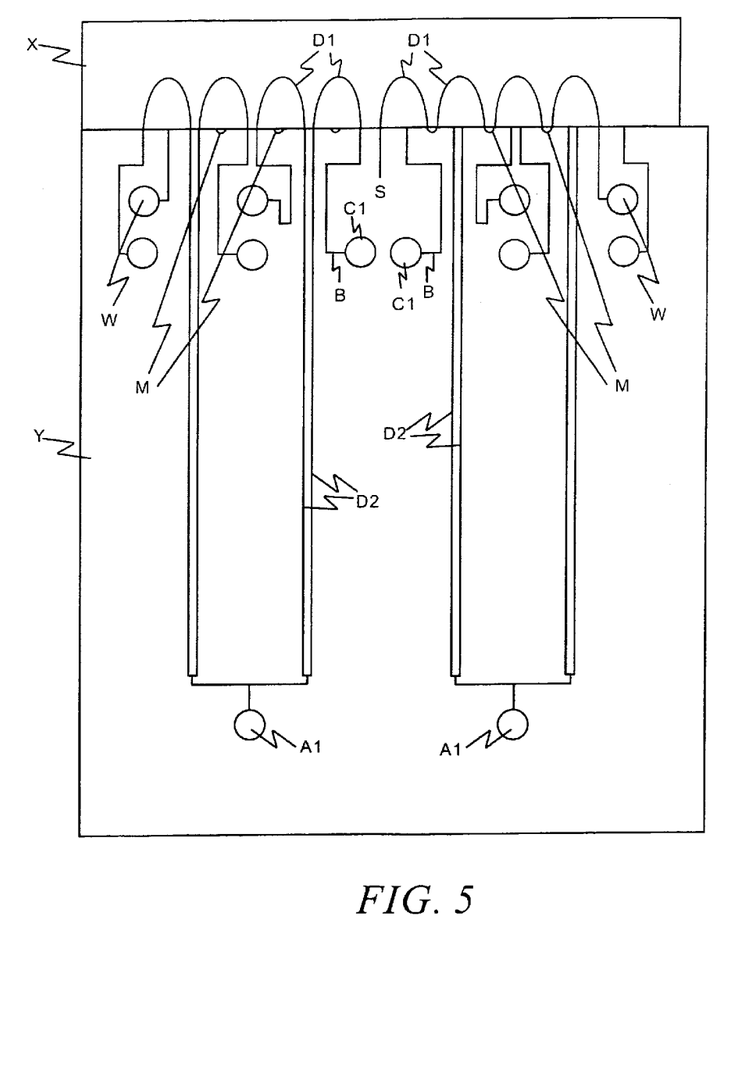

In additional embodiment, the interface in FIG. 2 can be slightly modified to FIG. 5 to integrate HPLC as the first separation dimension to CGE, CE or CEC as the second separation dimension for continuous 2-D separation. Referring to FIG. 5, HPLC effluent S flows into the continuous channel (composed by the repeating units of D1 and M channels) on the right-hand side. As the effluent front approaches the last D1 channel (before entering waste container W), the middle piece Y is switched right to another position (figure not shown). The continuous channel on the right-hand side is broken into pieces of D1 and M channels and D1 channels are inserted between cathode channels B and separation channels D2. HPLC separated bands in D1 channels are injected into D2 channels on the right-hand side for the second-dimensional separation. Meanwhile, channels D1 and M on the left-hand side are connected into a continuous channel and HPLC effluent S is directed into this channel. As the effluent front approaches the last D1 channel (before entering waste container W) on the left-hand side, the middle piece Y is switched left to the original position (FIG. 5). The HPLC separated bands in the D1 channels on the left-hand side are injected into the according D2 channels for the second-dimensional separation. These operations are repeated until the completion of the HPLC (the first-dimensional) separation.

In conventional continuous 2-D separations, it is required that separation of the second dimension should be considerably faster than that of the first dimension in order to obtain meaningful 2-D separation data. Often, separation of the first dimension is deliberately slowed down and stopped-flow technique is occasionally used in the first separation dimension so that the separation of the second-dimension can catch up. This strategy not only reduces the overall throughput but also sacrifices the resolution of the first-dimension. The proposed approach virtually eliminates this requirement because the separation "speed" of the second dimension is picked up through parallel-channel operations. Theoretically, the continuous channel can be made sufficiently long to hold all the effluent of the first-dimensional separation.

Figure 6:
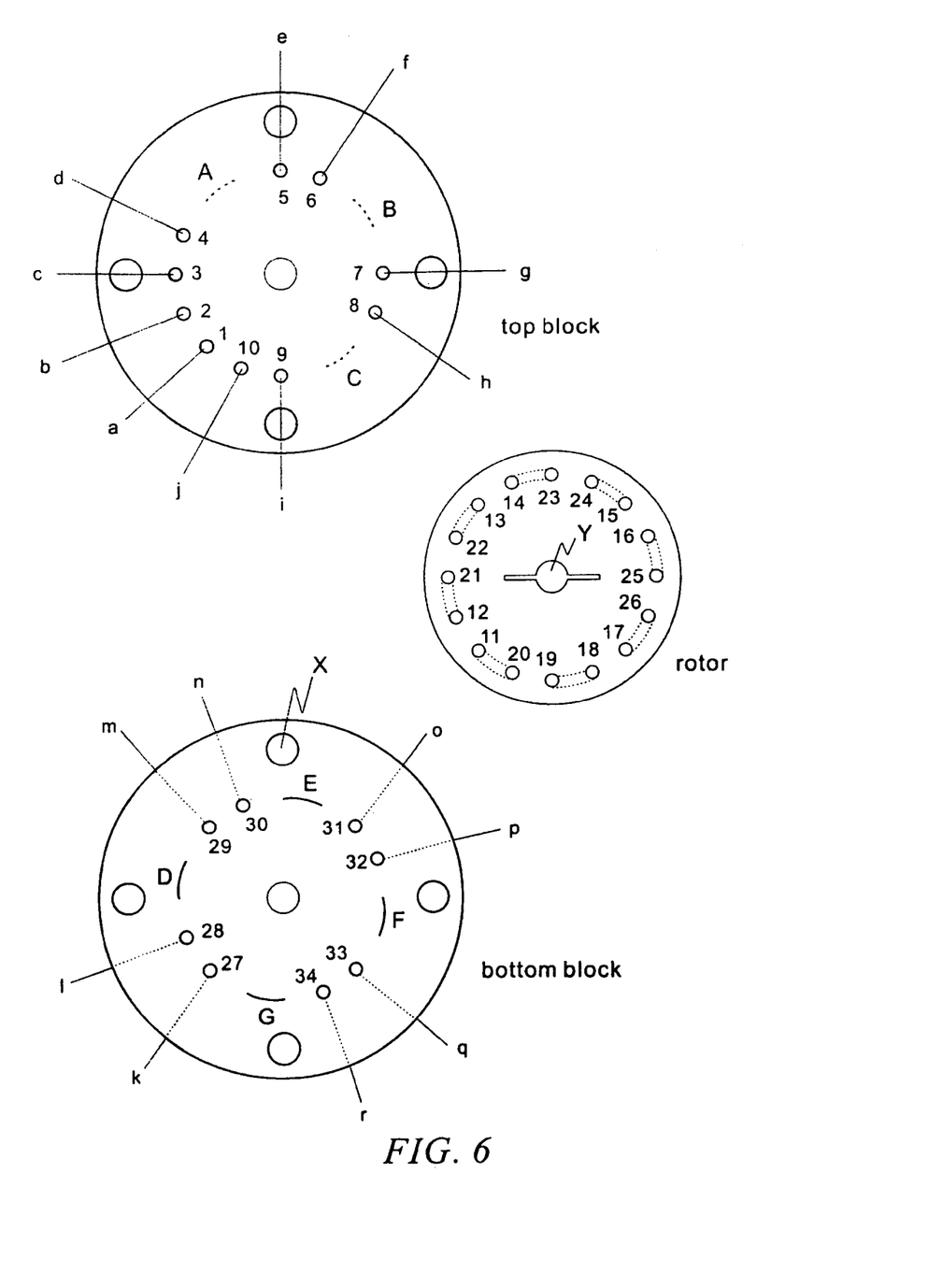

In another embodiment, movement of the middle piece Y in FIG. 1 can be achieved through a rotary motion. FIG. 6 presents a schematic diagram that entails how IEF as the first separation dimension is integrated with CGE, CE or CEC as the second separation dimension. Referring to the top block, capillary tubes a–j are connected to holes 1–10 from the top side of the block and grooves A–C are created on the bottom side of the block. Referring to the bottom block, capillary tubes k–r are connected to holes 27–34 from the bottom side and grooves D–G are created on the top side of the block. When the three pieces are assembled, the rotor is sandwiched by the top and bottom blocks. The four large holes X around the circumference on both top and bottom blocks are used to assemble and tighten the three pieces and the holes in the middle to facilitate the rotation of the rotor. Referring to the rotor, tilted holes are constructed in it. The hole-openings 11–18 are on the top side and 19–26 on the bottom side of the rotor. The tilted holes (the connection of the top openings to the bottom ones) are indicated by the dashed lines. The structure in the middle of the rotor is used to facilitate the rotation of the rotor.

As the interface is assembled such that holes 1 and 2 on the top block, openings 11 and 12 on the rotor and holes 27 and 28 on the bottom block are aligned. Hole-openings 13–14 are automatically aligned with groove A, 15–16 with groove B, and 17–18 with groove C. Meanwhile, hole openings 19–20 are aligned with groove G, 21–22 with groove D, 23–24 with groove E, and 25–26 with grooves F. When the interface is aligned at this position, capillary tubes a and b are connected into a single continuous tube. The narrative connection goes along: capillary tube a to hole 1 on the top block, to tilted hole 11–20 on the rotor, to groove G on the bottom block, to tilted hole 19–18 on the rotor, to groove C on the top block, to tilted hole 17–26 on the rotor, to groove F on the bottom block, to tilted hole 25–16, to groove B on the top block, to tilted hole 15–24 on the rotor, to groove E on the bottom block, to tilted hole 23–14, to groove A on the top block, to tilted hole 13–22, to groove D on the bottom block, to tilted hole 21–12 on the rotor, to hole 2 on the top block, and finally to capillary b. IEF separation of proteins is performed in this continuous tube.

After IEF is carried out, the rotor is switched to another position in which holes 1 and 2 on the top block, openings 19 and 20 on the rotor and holes 27 and 28 on the bottom block are aligned. Then, capillary tube c, tilted channel 11–20 and capillary tube l are connected. So are capillary d, tilted hole 12–21 and capillary m; capillary e, tilted hole 13–22 and capillary n; and so on. The IEF separated protein bands in the tilted holes are inserted into their according capillary tubes (e.g. rotor hole 12–21 is inserted between capillary tubes d and m) and the second-dimension separation are then performed. Preparation for the second separation dimension is carried out when the interface is at this position before IEF is performed. Grooves A–G are preferred short and shallow since samples in these grooves are not used for the separations.

Figure 7:
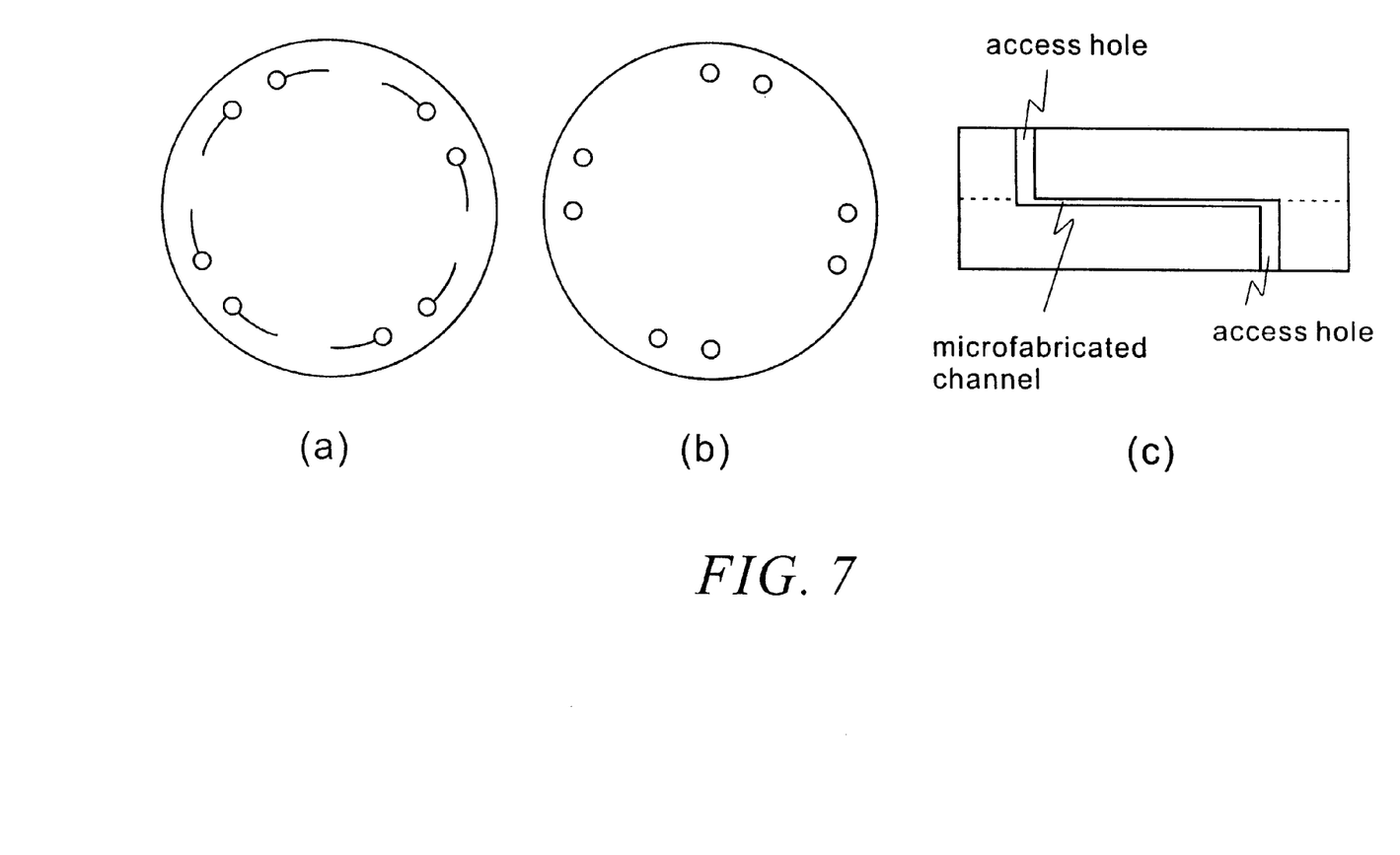

In additional embodiment, the rotor with the "tilted holes" is microfabricated because it is challenging to drill tilted holes on the rotor precisely and accurately. FIG. 7 presents the formation of "tilted holes" on a rotor. Grooves are first fabricated on one wafer and access holes are drilled on one end of each groove (FIG. 7a). On the cover wafer, access holes are drilled in positions corresponding to the other end of each groove (FIG. 7b). When these two wafers are aligned and bonded, the tilted holes are formed. FIG. 7c presents a expanded cross-section view of such a "tilted hole". The "tilted hole" is actually a Z-shaped channel formed by two access holes and a microchannel.

Figure 8:
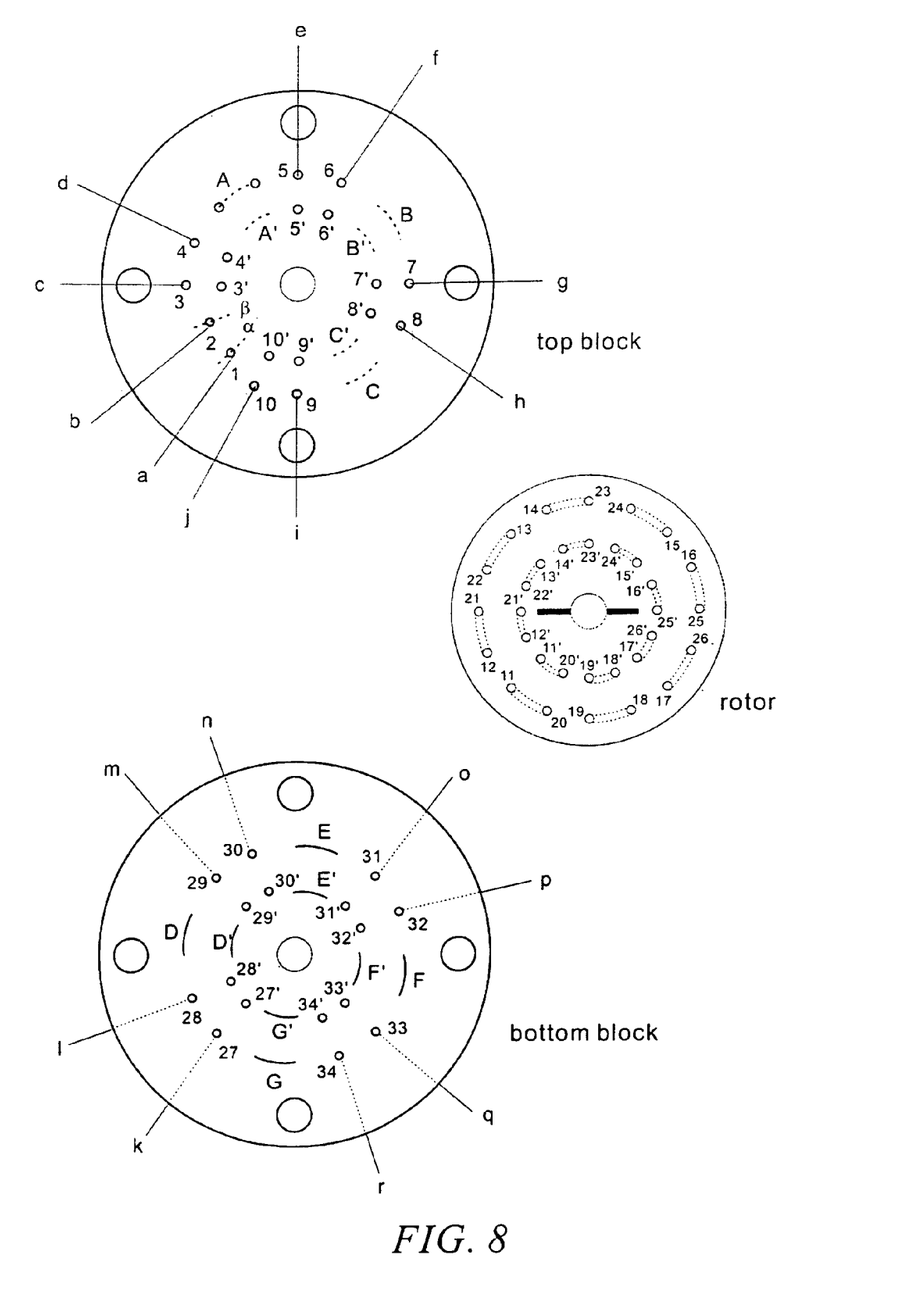

In another embodiment, the above interface (as shown in FIG. 6) can be slightly modified to incorporate HPLC as the first-separation dimension with CE, CEC or CGE as the second separation dimension. Referring to FIG. 8, there are two sets of holes and grooves. Holes 1 and 2 on the top block are located between these two sets of holes and grooves, and two extra grooves α and β are created in the radial direction on the bottom surface of the top block. Please notice that the "tilted holes" or the Z-shaped channels in the rotor are spatially cross each other, e.g. hole 11–20 is from top side to the bottom side of the rotor, while hole 11'–20' from the bottom side to the top side. HPLC effluent is directly introduced into capillary tube a. When holes 3 and 4 on the top block, openings 21 and 22 on the rotor, and the ends of groove D on the bottom block are aligned, the effluent flows through capillary a, hole 1 and groove α on the top block, channel 11–20 on the rotor, groove G on the bottom block, channel 19–18 on the rotor, groove C on the top block, channel 17–26 on the rotor, groove F on the bottom block, channel 25–16 on the rotor, groove B on the top block, hole 15–24 on the rotor, groove E on the bottom block, channel 23–14 on the rotor, groove A on the top block, channel 13–22 on the rotor, groove D on the bottom block, channel 21–12 on the rotor, groove β and hole 2 on the top block, and finally out to capillary b.

Before the effluent front gets into capillary b, the interface is switched to another position in which holes 3 and 4, openings 11 and 12 on the rotor and the ends of groove D on the bottom block are aligned. Channel 11–20 is inserted between capillaries c and l and the effluent inside channel 11–20 is injected into the capillary for the second-dimensional separation. Similarly, the effluents in the other channels are injected into their according capillaries for the second-dimensional separations.

While the second-dimensional separations are performed in the capillaries on the outer circle, the HPLC effluent flows through hole 1 and groove α on the top block into the channels and grooves on the inner circle. Before the effluent gets out into capillary b, the interface is switched back to its original position. Effluents in the channels on the inner circle are injected into their according capillaries for the second-dimensional separations while HPLC effluent flows back into the channels and grooves on the outer circle. These operation steps are repeated until the HPLC separation (the first-dimensional separation) is complete.

Figure 9:
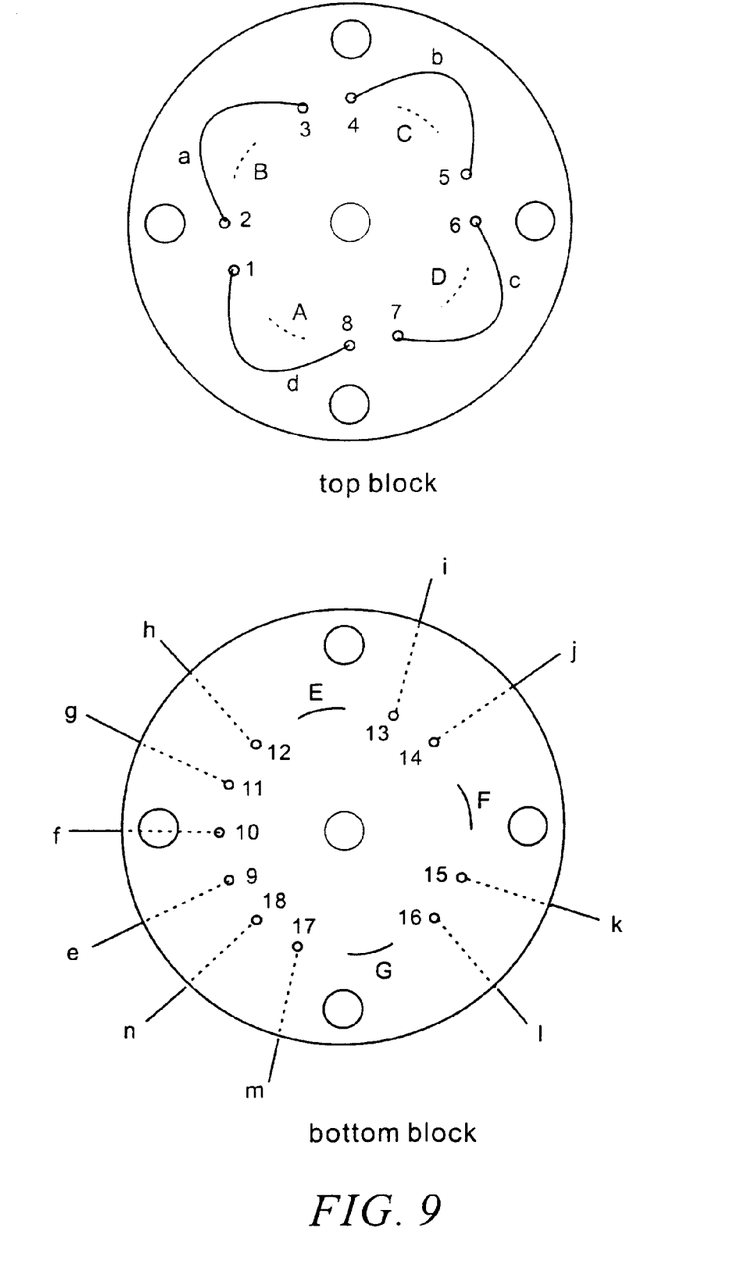

The above interface (in FIG. 6 or FIG. 8) comprises three pieces. In additional embodiment, the first separation dimension can be integrated with the second separation dimension using a two-piece rotary interface. The fundamental concept is the same as that of FIG. 2 or 5. FIG. 9 is a schematic representation of the incorporation of IEF as the first separation dimension to CGE, CE or CEC as the second separation dimension. When holes 1 and 2 on the top block are aligned with 9 and 10 of the bottom block, capillary e on the bottom block is connected sequentially to capillary d on the top block, groove G on the bottom block, capillary c on the top block, groove F on the bottom block, capillary b on the top block, groove E on the bottom block, capillary a on the top block, and finally capillary f on the bottom block. This continuous channel can be used for the first-dimensional separation such as IEF.

After the first-dimensional separation is carried out, the interface is switched to another position so that holes 1 and 2 on the top block are aligned with holes 11 and 12 on the bottom block. Capillary d on the top block is inserted between capillaries g and n on the bottom block and, subsequently, the analytes in capillary d is injected into the capillary for the second-dimensional separation. Similarly, capillary a, b and c on the top block are respectively inserted between capillaries h and i, j and k, and l and m for the second-dimensional separations.

Figure 10:
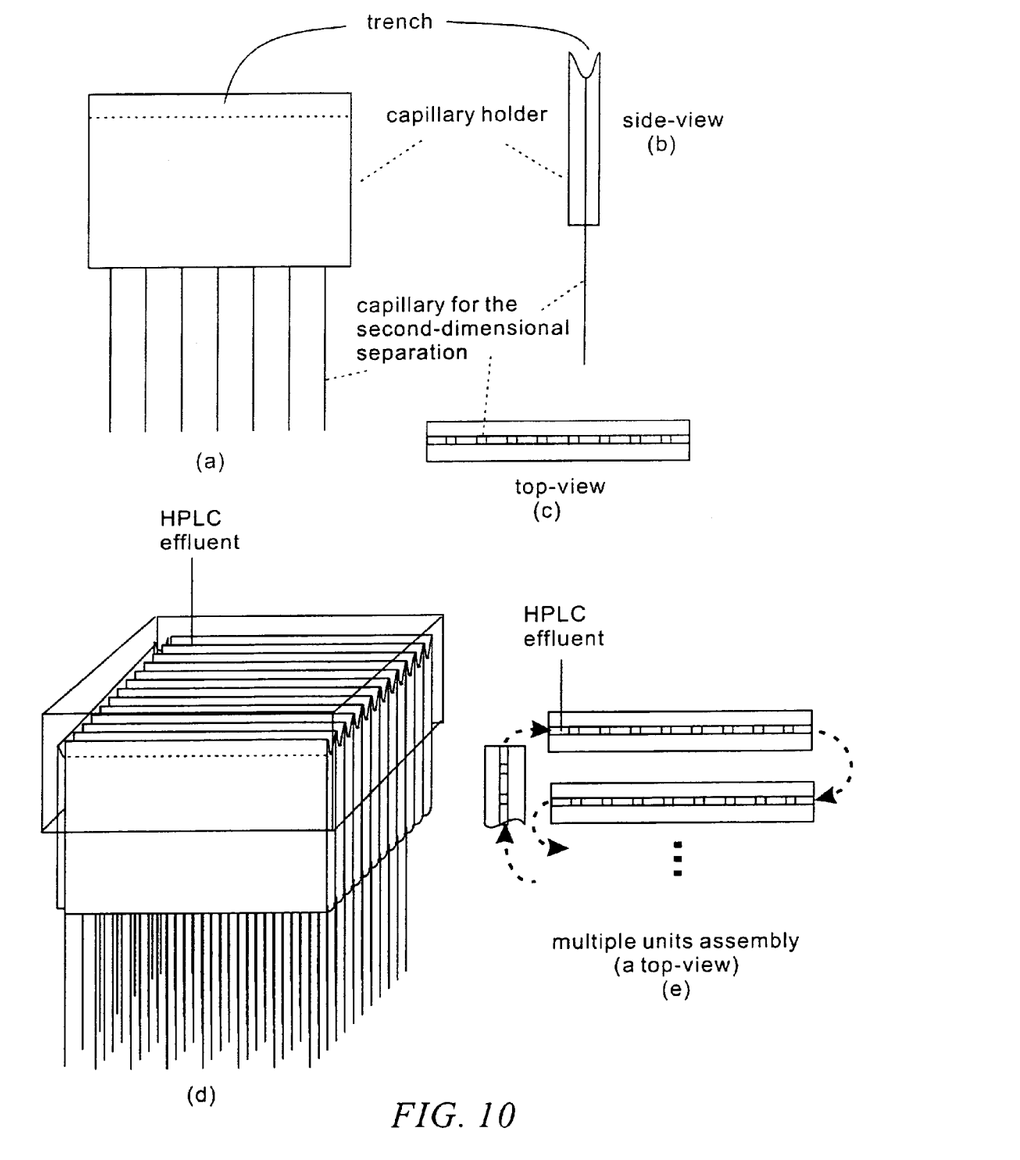
FIG. 10. A schematic representation of an integration interface (1-piece) in which the partially separated sample from the first separation dimension is sequentially introduced to the separation columns of the second separation dimension FIG. 11. A schematic representation of a circular integration interface (1-piece) in which the partially separated sample from the first separation dimension is sequentially introduced to the separation columns of the second separation dimension FIG. 12. A schematic representation of the integration of the second dimension separation with chemical reaction, MS detection, or fraction collection

In another embodiment, two separation dimensions can be integrated using a one-piece interface. Partially separated sample after the first dimensional separation, such as IEF, HPLC and CE, are directly introduced to the separation columns of the second separation dimension as schematically presented in FIG. 10. Referring to FIG. 10a, the sample inlet ends of the columns for the second-dimensional separation are held together densely through a column holder. On the top of the holder (referring to FIGS. 10b and 10c), there is a "V-shaped" trench across the entire holder. The column ends are connected to the trench from the bottom of the trench. FIG. 10d presents an assembly of multiple holders for the integration of the first with the second separation dimension. The head of the assembly is used to form the bottom of a container containing background electrolyte solution for the second-dimensional separation. Of course, the hydraulic pressure across the capillaries will be maintained minimal or zero, although the capillary end are shown at different elevation levels in FIG. 10. The partially separated sample of the first separation dimension, such as HPLC effluent, is moving along the trenches of the holders while voltage is applied across the columns for the second dimensional separations. The movement of the sample outlet of the first separation dimension can be simply a continuous motion. Preferably, it should be stepped motions from column to column of the second separation dimension. FIG. 10e shows the direction and trace in which the effluent outlet travels. Because many capillaries are used for the second dimensional separation, the separation speed of the second-dimensional separation doesn't have to be very fast. This dramatically increases the number of choices for the second-dimensional separation.

Figure 11:
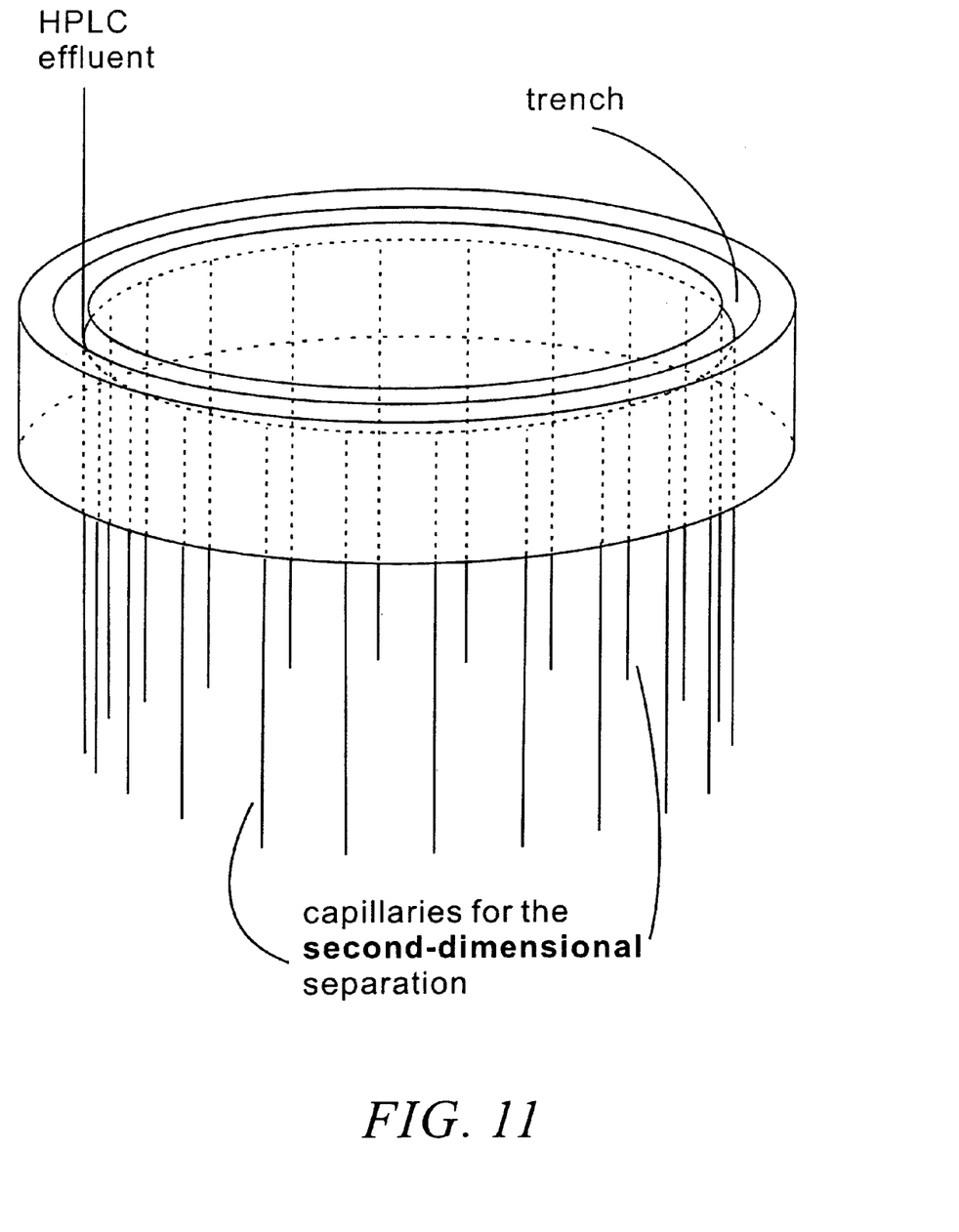

In preferred embodiment, a round trench can be made on a block as schematically presented in FIG. 11. Columns, such as capillaries, of the second dimensional separation are introduced to the trench from the bottom. In the actual device, there will be more than 4 columns, preferably more than 8 columns, preferably more than 24 columns, preferably more than 96 columns, and preferably more than 384 columns. Pre-separated sample from the first separation dimension, such as HPLC effluent, is delivered directly to the inlets of the second separation columns to perform the second dimension separation. It is worthy pointing out that the second-dimensional separations occur at different times in different capillaries. This can be corrected conveniently using a software program.

Figure 12:
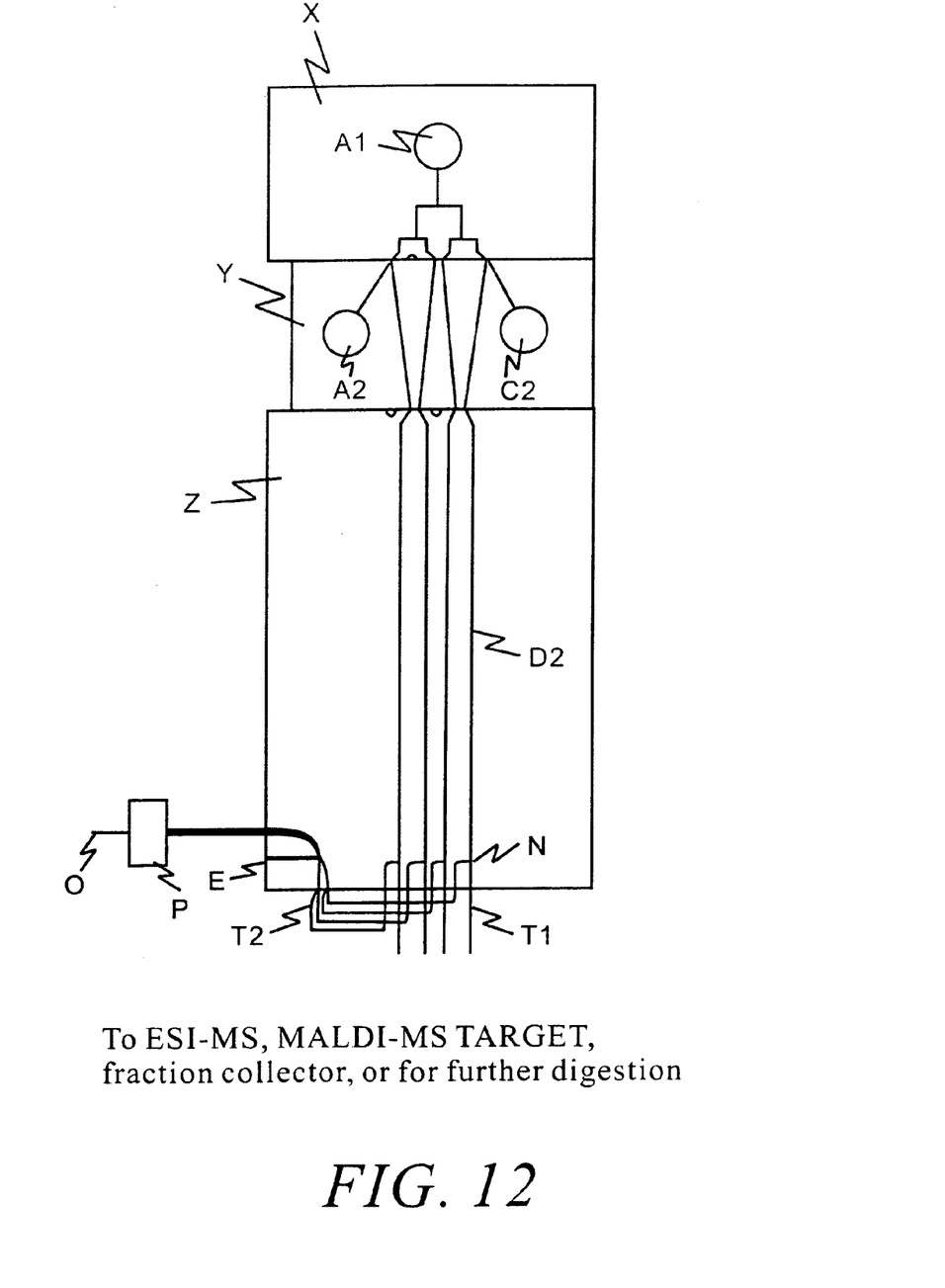

In a recent publication (Yao, et al Proc. Natl. Acad. Sci. USA 1999, 96, 5372–5377), β-galactosidase (MM=116 kDa) has been driven out of a 4.5-cm-long column filled with a commercial gel (SDS 14-200 gel, Beckman Coulter) in 30 s. In a different paper (Bousse, et al., Anal. Chem. 2001, 73, 1207–1212), Myosin (200 kDa) has been electrophoresed out of a ~1.25-cm-long chip-channel filled with 3.25% polydimethylacrylamide in 4 s. In another article (Jin, et al. Anal. Chem. 2001, 73, 4994–4999), Myosin has been electrophoretically driven out of a 7- and a 19-cm-long columns filled with Bio-Rad gel in about 200 s and 12 mm, respectively. In a particular embodiment of this invention, the separated proteins/peptides from the second dimensional separation will be driven out to perform further chemical reaction and/or analysis. FIG. 12 is a schematic representation of a 2-D separation device coupled to a post-column reactor, a fraction collector, an MS detector or a MALDI-MS sample target. In this scheme, the conventional electrode reservoir A1 (referring to FIG. 1) is replaced by a bubbleless electrode E (disclosed in a patent application, U.S. patent application Ser. No. 10/076,170). An auxiliary electrolyte solution (for ESI-MS), a matrix containing solution (for Maldi-MS), or a digestion solution (for digestion) O is introduced through a pump P to separation channels D2 at positions N. Capillary tubes T1 are connected to separation channels D2 to facilitate ESI or sample deliveries to a Maldi-MS target or a fraction collector. Capillaries T2 are used to make both fluidic and electric connections between D2 channels and the external solutions and the bubbleless electrode. All these capillaries should have the same diameter and length to ensure equal field strength and flow resistance in separation channels D2 and the capillary tubes T1.

All of the methods and apparatus disclosed and claimed herein can be made and executed without undue experimentation in light of the present disclosure. While the invention has been described with respect to the described embodiments in accordance therewith, it will be apparent to those skilled in the art that various modifications and improvements may be made without departing from the scope and spirit of the invention. For example, it will be apparent to those of skill in the art that variations may be applied to the methods and apparatus and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims. Accordingly, it is to be understood that the invention is not to be limited by the specific illustrated embodiments, but only by the scope of the appended claims.

The invention claimed is:

1. A device for high-resolution sample separation, comprising:
   a substrate that comprises at least first and second blocks that are configured to slide relative to each other from a first position to a second position;
   at least a first separation channel defined on the first block containing separation medium;
   at least a second separation channel defined on the second block containing separation medium;
   wherein at the first position, the device is configured for separation of a sample along the first separation channel containing separation medium, whereby the sample is partially separated along the first channel, and
   wherein at the second position, the device is configured with at least a section of the first channel, less than entire length of first channel, in fluid communication with at least a section of the second channel for separation in said at least a section of the second channel at least a portion of the sample which is located in said at least a section of the first separation channel and has been partially separated in the first separation channel.

2. A method for high-resolution sample separation, comprising the steps of:
   providing a substrate comprising at least first and second blocks that are configured to slide relative to each other;
   partially separating a sample in a first separation channel defined in the first block;
   sliding the first block relative to the second block; and
   effecting separation along a second separation channel defined in the second block a portion of the sample which is located in a section of the first separation channel and which has been partially separated in the first separation channel.

3. A microfluidic device, comprising:
   a reconfigurable substrate, configured for separation of a sample in a first and a second configurations;
   a first fluid channel defined on the substrate containing separation medium, for partial separation of the sample;
   a second fluid channel defined on the substrate containing separation medium, for further separation of a portion of the sample which has been partially separated in the first fluid channel, wherein at least a section of the first channel, less than entire length of first channel, is in fluid communication with at least a section of the second fluid channel in the second configuration of the substrate but not in fluid communication in the first configuration of the substrate.

4. The device as in claim 1, wherein at least one of the first and second separation channels is microfabricated on the respective first and second blocks.

5. The device as in claim 1, wherein at least one of the first and second blocks comprise glass or polymeric material, which may be one of plastic, PTFE (polytetrafluoroethylene), Nylon, PVC (polyvinyl chloride), PMMA (poly(methyl methacrylate)), polycarbonate, polystyrene, polypropylene, nitrocellulose, poly(ethylene terephthalate).

6. The device of claim 1, wherein at least one of the first and second channels comprises curved or straight channel sections.

7. The device of claim 1, wherein at least one of the first and second blocks comprises repeated units of channel sections.

8. The device of claim 1, wherein at the first position, the device is configured for at least one of IEF (Isoelectric focusing), capillary electrophoresis (CE), HPLC, SEC (size exclusion chromatograph), IC (ion-exchange chromatograph) or affinity chromatograph.

9. The device of claim 1, wherein the first and second separation channels each comprises at least two channel sections, wherein at the second position, one of the two channel sections of the first separation channel is in fluid communication with one of the two channel sections of the second separation channel, and the other one of the two channel section of the first separation channel is in fluid communication with the other one of the two channel sections of the second separation channel.

10. The device of claim 1, wherein separated samples in the second separation channel are subject to a detection system, which comprises at least one of MALDI-MS and ESI-MS, or a fraction collector.

11. The device of claim 1, wherein separated samples in the second separation channel are subject to a device for chemical reaction including protein digestion.

12. The device of claim 1, wherein the first and second blocks are configured to slide relative to each other by relative rotation.

13. The method as in claim 2, wherein at least one of the first and second separation channels is microfrabricated on the respective first and second blocks.

14. The method as in claim 2, wherein at least one of the first and second blocks comprise glass or polymeric material, which may be one of plastic, PTFE (polytetrafluoroethylene), Nylon, PVC (polyvinyl chloride), PMMA (poly(methyl methacrylate)), polycarbonate, polystyrene, polypropylene, nitrocellulose, poly(ethylene terephthalate).

15. The method as in claim 2, wherein the step of partially separating the sample in the first separation channel comprises at least one of IEF (Isoelectric focusing), capillary electrophoresis (CE), HPLC, SEC (size exclusion chromatograph), IC (ion-exchange chromatogaph) or affinity chromatograph.

16. The method as in claim 2, further comprising subjecting the separated samples in the second separation channel to detection, which comprises at least one of MALDI-MS and ESI-MS, or a fraction collector.

17. The method as in claim 2, further comprising subjecting the separated samples in the second separation channel to chemical reaction, including protein digestion.

18. The method as in claim 2, wherein the step of sliding the first block relative to the second block comprises relative rotating the first block relative to the second block.

19. The device as in claim 3, wherein the reconfigurable substrate comprises a first block on which the first fluid channel is defined, and a second block on which the second fluid channel is defined.

20. The device as in claim 19, wherein the first block is movable relative to the second block, by relative sliding or rotation.

21. The method of claim 2, wherein the second separation channel comprises a plurality of separate channel sections, and wherein the sample is partially separated into different portions at different sections of the first separation channel, and the different portions of partially separated sample at the different sections of the first separation channel are simultaneously separated along the plurality of different channel sections of the second separation channel.

* * * * *